(12) United States Patent
Winer et al.

(10) Patent No.: US 6,620,816 B2
(45) Date of Patent: Sep. 16, 2003

(54) METHOD FOR TREATING TUMORS BY THE ADMINISTRATION OF TEGAFUR, URACIL, FOLINIC ACID, AND CYCLOPHOSPHAMIDE

(75) Inventors: Eric P. Winer, Wellesley, MA (US); Craig A. Bunnell, Brookline, MA (US); Jody Ressler-Tatro, Kensington, CT (US); Terry S. Dugan, Plainsboro, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/126,745

(22) Filed: Apr. 19, 2002

(65) Prior Publication Data

US 2002/0187956 A1 Dec. 12, 2002

Related U.S. Application Data

(60) Provisional application No. 60/286,729, filed on Apr. 26, 2001.

(51) Int. Cl.$^7$ .................... A61K 31/505; A61K 31/495; A01N 57/36
(52) U.S. Cl. ............................ 514/256; 514/73; 514/50; 514/105; 514/249
(58) Field of Search .................... 514/50, 247, 249, 514/274, 44, 105, 73, 256; 424/93.1, 601

(56) References Cited

U.S. PATENT DOCUMENTS

| | | | |
|---|---|---|---|
| 4,328,229 A | | 5/1982 | Fujii et al. |
| 5,534,513 A | * | 7/1996 | Junji et al. .................. 514/249 |
| 5,688,773 A | * | 11/1997 | Chiocca et al. ............ 424/93.1 |

OTHER PUBLICATIONS

Haga, S. et al "Antitumor Efficacy of Combination Chemotherapy with UFT and Cyclophosphamide against Human Breast Cancer Xenografts in Nude Mice", Anticancer Research, 1999, vol. 19 (3A), 1791–1796.*
Fukuda, M. et al "Combination Therapy for Advanced Breast Cancer: Cyclophosphamide, Doxorubicin, UFT, and Tamoxifen" Oncology, 1999, vol. 13, No. 7 (suppl. 3), 77–81.*
Smith, I.E. "Epirubicin, Cyclophosphamide and UFT Plus Oral Calcium Folinate in Advanced Breast Cancer", Oncology, 1999, vol. 13, No. 7 (suppl. 3), 82–85.*
Y. Tanaka, et al.; Int. J. Cancer 1999, vol. 83, pp. 127–134.

* cited by examiner

*Primary Examiner*—James O. Wilson
*Assistant Examiner*—Ganapathy Krishnan
(74) *Attorney, Agent, or Firm*—Maureen S. Gibbons

(57) ABSTRACT

This invention provides a method of treating a tumor in a warm-blooded animal, including humans, by administering, in combination, an anti-tumor effective amount of tegafur, uracil, folinic acid or pharmaceutically acceptable salt thereof and cyclophosphamide.

7 Claims, No Drawings

METHOD FOR TREATING TUMORS BY THE ADMINISTRATION OF TEGAFUR, URACIL, FOLINIC ACID, AND CYCLOPHOSPHAMIDE

This application claims benefit to provisional application U.S. Ser. No. 60/286,729 filed Apr. 26, 2001. The entire teachings of the referenced applications are incorporated herein by reference.

FIELD OF THE INVENTION

The present invention is directed to the administration to a warm blooded animal including humans of the combination of tegafur, uracil, and folinic acid and its administration with cyclophosphamide for the treatment of tumors.

BACKGROUND OF THE INVENTION

5—Fluorouracil (5—FU) is a known anti-tumor agent. The combination of 5-fluorouracil and folinic acid is a known treatment for cancer including adenocarcinoma of the female breast. Tegafur (1-(2-tetrahydrofuryl)-5-fluorouracil) is a prodrug of 5-fluorouracil. In vivo, 5-fluorouracil is rapidly inactivated by the enzyme dihydropyridine dehydrogenase (DPD). Uracil competitively inhibits DPD metabolism of 5—FU generated from tegafur. Thus, coadministration of uracil with tegafur results in higher exposures of active 5—FU as compared to tegafur alone. It is also known that 5-fluorouracil cannot be administered orally.

U.S. Pat. No. 4,328,229 discloses an anti-cancer composition containing 1-(2-tetrahydrofuryl)-5-fluorouracil ("tegafur") and uracil. The composition is used for delivery of 5-fluorouracil to a tumor sensitive to 5-fluorouracil in a warm-blooded animal. It is disclosed that the composition can be co-administered in a variety of dosage forms including an oral dosage form.

U.S. Pat. No. 5,534,513 discloses an anti-tumor composition containing tegafur and uracil in a molar ratio of 1:4. This anti-tumor composition is stated to be further potentiated by the administration of folinic acid or a pharmaceutically acceptable salt thereof. It is disclosed in the '513 patent that the combination can be administered in a variety of dosage forms including an oral dosage form.

Cyclophosphamide has been shown useful for the treatment of certain malignancies. For decades, cyclophosphamide has remained one of the most commonly used chemotherapeutic agents for the treatment of breast cancer. Cyclophosphamide acts primarily by alkylation, however it also inhibits DNA synthesis. It is known that cyclophosphamide may be administered orally or intravenously. The primary side effects of oral administration are myelosuppression and nausea.

It has been observed by Applicants that 5-fluorouracil can enhance the activity of cyclophosphamide. However, because 5-fluorouracil cannot be administered orally, the mode of administration for this combination therapy treatment requires a more invasive form of administration such as by intravenous injection, and therefore typically requires administration by trained medical personnel.

It would be an advance in the art of treating tumors, especially breast cancer tumors, if a therapy could be developed employing the administration of cyclophosphamide and 5-fluorouracil, especially where 5-fluorouracil may be administered in a convenient oral dosage form.

SUMMARY OF THE INVENTION

The present invention is generally directed to the administration of tegafur, uracil, folinic acid or a pharmaceutically acceptable salt thereof, and cyclophosphamide in suitable dosage forms to warm-blooded animals, including humans, for the treatment of tumors, especially breast cancer tumors. In a particular aspect of the invention, tegafur, uracil, folinic acid or a pharmaceutically acceptable salt thereof, and cyclophosphamide are administered in oral dosage form(s) to a warm-blooded animal, including humans, having a tumor. In a preferred form of the invention, tegafur and uracil are present in respective amounts sufficient for tegafur to effectively and efficiently convert to 5-fluorouracil. In a particularly preferred embodiment of the invention, tegafur and uracil are present in a molar ratio of about 1:4 (hereinafter referred to as "UFT").

There is also disclosed a method of treating cancer by orally administering an anti-tumor effective amount of the combination of tegafur and uracil, preferably as UFT, and folinic acid or a pharmaceutically acceptable salt thereof to a warm-blooded animal, including humans, having a tumor who is undergoing cyclophosphamide therapy treatment.

DETAILED DESCRIPTION OF THE INVENTION

The combination of tegafur and uracil in amounts sufficient to convert tegafur to 5-fluorouracil (preferably a molar ratio of about 1:4) can be administered orally. It was discovered that administration of this combination produced sufficient 5-fluorouracil and along with cyclophosphamide would provide a potent and effective treatment of tumors especially those associated with breast cancer.

The oral dosage forms of tegafur, uracil, folinic acid or a pharmaceutically acceptable salt thereof and cyclophosphamide used in the present invention provide significant advantages over administering the combination of these cancer treating agents by other modes of administration which are more invasive and discomforting. For example, there is realized a reduction in the cost of therapy because skilled medical personnel are not required to administer the drug. In addition, there are psychological benefits afforded to a patient by taking an oral medication over more invasive therapies typically associated with cancer treating agents.

In one oral dosage form of the present invention, tegafur, uracil, and folinic acid, preferably provided as the calcium salt "calcium folinate," are present in a single oral dosage form. Alternatively, and preferably, tegafur and uracil are provided in a first oral dosage form, and folinic acid, preferably provided as calcium folinate, is provided in a second oral dosage form. The dosage of each active ingredient for administration on a daily basis is from about 0.1 to 100 mg/kg/day, preferably about 1 to 30 mg/kg/day for tegafur. The preferred dosage for uracil is from about 1 to 50 mg/kg/day. For UFT, i.e. the 1:4 combination of tegafur and uracil, the dosage is from about 100 to 500 mg/m$^2$/day based on tegafur, preferably from about 200 to 300 mg/m$^2$/day based on tegafur, more preferably about 200 mg/m$^2$/day based on tegafur. Folinic acid or a pharmaceutically acceptable salt thereof may be administered in an amount from about 0.1 to 500 mg/kg/day, but preferably is administered as calcium folinate in a fixed dose of about 60 or 90 mg/day. The oral dosage form(s) may be administered in a single dose or in divided doses typically up to 3 times a day.

The respective dosages of UFT and calcium folinate specified above may be administered together as separate agents in an oral form such as ORZEL™. ORZEL™ is an oral combination of UFT and calcium folinate which are supplied to the patient together, but as separate agents. When orally administered to a patient, ORZEL™ provides a steady, continuous source of 5—FU in the patient's bloodstream. ORZEL™ has further been demonstrated to be less toxic than conventional bolus infusional 5—FU. In a preferred embodiment of the present invention UFT is provided in a gelatin capsule shell which comprises 100 mg of tegafur, 224 mg of uracil, plus inactive ingredients including low substituted hydroxypropyl cellulose and sodium lauryl sulfate.

Cyclophosphamide is typically administered orally, such as in the form of a pill, tablet or capsule, however cyclophosphamide may also be administered by other modes including intravenous injection. In a preferred embodiment of the present invention, cyclophosphamide is orally administered. Based on body surface area, the oral dosage of cyclophosphamide may range from about 10 to 500 mg/m$^2$/day, preferably from about 50 to 300 mg/m$^2$/day, more preferably about 100 mg/m$^2$/day.

Those of ordinary skill in the art would have the knowledge to adjust the above stated dosage ranges for UFT, folinic acid or a pharmaceutically acceptable salt thereof, and cyclophosphamide as needed based on body surface area, tumor type, stage of the tumor, and/or drug tolerance of the patient in the event of toxicity and side effects. In accordance with the present invention, the combination of tegafur and uracil (e.g. UFT) results in a sufficient amount of 5-fluorouracil available in combination with cyclophosphamide to provide an effective treatment of tumors, especially breast cancer tumors in a non-invasive manner.

In a preferred form of the invention, the method of treating a tumor in a warm-blooded animal, including humans, comprises administering the active agents in a regimen typically based on a twenty-eight day cycle. By way of example, cyclophosphamide may be administered at a dose of about 100 mg/m$^2$/day on days 1 to 14 of the twenty-eight day cycle, and UFT at a dose of 200 mg/m$^2$/day based on tegafur and calcium folinate at a dose of 60 mg/day may be administered on days 1 to 21 followed by no administration of the active agents on days 22–28. The twenty-eight day cycle may be repeated as necessary. The cyclophosphamide is preferably administered orally.

The dosage forms may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The dosage forms for all oral administration include tablets, powders, granules, and the like. Excipients and additives which may be used include, but are not limited to, lactose, sucrose, sodium chloride, glucose, urea, starch, calcium, kaolin, crystalline cellulose, salicylic acid, methylcellulose, glycerol, sodium alginate, arabic gum and the like. Conventional binders may be used such as glucose solutions, starch solutions, gelatine solutions, and the like. Disintegrators may be used including, but not limited to, dry starch, sodium alginate, agar powder, calcium carbonate, and the like. Absorbents which may be used include, but are not limited to, starch, lactose, kaolin, bentonite, and the like, Lubricants which may be used include, but are not limited to, purified talc, stearic acid salts, boric acid powder, polyethylene glycol and the like.

The following examples are exemplary of the claimed invention, but are not intended to limit the invention as encompassed by the full disclosure of the invention set forth herein.

EXAMPLE 1

This study assessed the in vivo maximum tolerated dose (MTD), the side effect profile and the dose limited toxicity (DLT) of cyclophosphamide combined with UFT (tegafur and uracil in a molar ratio of 1:4) plus calcium folinate in patients with metastatic breast cancer (MBC).

A standard phase I trial was conducted with escalating doses of UFT as shown in Table 1 below with a fixed dose of calcium folinate (leucovorin) at 60 mg/day (30 mg BID) and cyclosphosphamide at 100 mg/m$^2$/day. Entry criteria for the study included, but was not limited to, a histological or cytological confirmed metastatic breast cancer, no concurrent radiotherapy treatment, less than 3 prior chemotherapy treatments for metastatic disease, ECOG performance status of 0–2, no brain metastatic disease, adequate hematological, renal and hepatic function, and no prior infusional or oral 5—FU agent.

TABLE 1

| Dose Level (mg/day) | Cyclophosphamide Dosage (mg/m$^2$/day) | UFT Dosage (mg/m$^2$/day) | Calcium Folinate Dosage (mg/day) |
|---|---|---|---|
| 1 | 100 | 200 | 60 |
| 2 | 100 | 250 | 60 |

The treatments were given to human patients on a four-week cycle until progressive disease or unacceptable toxicity occurred. UFT and calcium folinate were given orally on days 1–21 of each cycle; cyclophosphamide was administered orally on days 1–14 of each cycle. The study continued to each progressive level until the maximum tolerated dose (MTD) was experienced.

The MTD was defined as the dose level at which greater than 1/3 or 2/6 of the patients experienced a dose limiting toxicity (DLT) during the first cycle of treatment.

The DLT was defined as follows:
a. Grade 3/4 neutropenia complicated by fever greater than 38° C., I.V. antibiotics or grade 3/4 diarrhea, or
b. Grade 4 thrombocytopenia prolonged or complicated by bleeding or requiring platelet transfusion, or
c. Grade 3/4 neutropenia or thrombocytopenia for more than 7 days, or
d. Grade 3/4 non-hematological toxicity with the exception of alopecia, nausea and vomiting, or
e. Grade greater than or equal to 2 renal, hepatic, cardiac or pulmonary toxicity or
f. A treatment delay of greater than two weeks prior to the start of the next cycle of treatment.

Patients qualified for the test protocol if they met the following criteria:
Histological or cytological confirmed locally advanced or metastatic breast cancer
Measurable disease (>1 cm in at least one dimension)
Age >18 years; female
No more than two prior chemotherapeutic regimens in the metastatic setting
ECOG performance status 0 or 1, life expectancy >3 months
At least 3 weeks since administration of prior chemotherapy treatment, radiation treatment, surgery, or any investigational agent
No prior cyclophosphamide chemotherapy treatment within 6 months
Written informed consent Patients were disqualified for the test protocol if they had bowel obstruction, any condition which would affect cyclophosphamide, UFT and/or calcium folinate absorption, or more than 3 prior radiotherapy sessions unless associated with palliative or adjuvant therapy treatment of adenocarcinoma.

The treatment regimen was generally well tolerated by the patients. No dose-limiting toxicities were observed at dose level 1. Two patients at dose level 2 experienced DLT (grade 3 diarrhea). Dose level 1 was determined to be the maximum tolerated dose. More than 60 cycles (range 1–10+) have been administered, at dose level 1, to 13 patients. Toxicities have generally been limited myelosuppression, fatigue, and gastrointestinal symptoms. Of patients treated at dose level 1, 2/13 experienced grade 3 neutropenia, 1/13 experienced grade 3 leukopenia, 2/13 experienced grade 3 fatigue, and 1/13 experienced grade 3 anorexia and diarrhea. Partial responses have been observed in 7/11 evaluable patients. Ten additional patients were treated at this level to further evaluate and characterize the toxicities and safety of the chemotherapeutic combination.

Based on the results of the study, the combination of UFT, calcium folinate (leucovorin) and cyclophosphamide administered to patients is observed to be a well tolerated, oral regimen which demonstrates anti-tumor activity.

What is claimed is:

1. A method of treating a tumor in a warm-blooded animal comprising administering to said warm-blooded animal in need thereof a combination of tegafur, uracil, and folinic acid wherein the combination of tegafur and uracil orally administered at a dosage of about 100 to 500 mg/m$^2$/day based on tegafur, folinic acid is orally administered at a dosage of about 0.1 to 500 mg/kg/day, and cyclophosphamide is orally administered at a fixed dosage of about 60 or 90 mg/day, and cyclophosphamide is orally administered at a dosage of about 10 to 500 mg/m$^2$/day.

2. The method of claim 1 wherein the combination of tegafur and uracil is orally administered at a dosage of about 200 mg/m$^2$/day based on tegafur, folinic acid is orally administered at a fixed dosage of about 60 or 90 mg/day, and cyclophosphamide is orally administered at a dosage of about 100 mg/m$^2$/day.

3. The method of claim 1 comprising administering tegafur, uracil, folinic acid or a pharmaceutically acceptable salt thereof and cyclophosphamide over a preselected period of time.

4. The method of claim 3 wherein the preselected period of time is twenty-eight days, and further comprising administering tegafur, uracil and folinic acid or a pharmaceutically acceptable salt thereof on days 1 through 21, and cyclophosphamide on days 1 through 14.

5. The method of claim 4, wherein the preselected period of time is repeated at least once.

6. The method of claim 1 wherein the tumor is a tumor of the breast.

7. The method of claim 1 wherein the warm-blooded animal is a human.

* * * * *